United States Patent
Roberts et al.

(10) Patent No.: US 6,541,424 B2
(45) Date of Patent: Apr. 1, 2003

(54) MANUFACTURE AND USE OF A HERBICIDE FORMULATION

(75) Inventors: Johnnie R. Roberts, Memphis, TN (US); Gregory C. Volgas, Bartlett, TN (US); James Thomas, Cordova, TN (US)

(73) Assignee: Helena Chemical Company, Collierville, TN (US)

(*) Notice: Subject to any disclaimer, the term of this patent is extended or adjusted under 35 U.S.C. 154(b) by 0 days.

(21) Appl. No.: 09/919,663

(22) Filed: Aug. 1, 2001

(65) Prior Publication Data

US 2002/0039970 A1 Apr. 4, 2002

Related U.S. Application Data

(60) Provisional application No. 60/223,390, filed on Aug. 7, 2000.

(51) Int. Cl.$^7$ .............................................. A01N 57/02
(52) U.S. Cl. ..................................................... 504/206
(58) Field of Search ........................................ 504/206

(56) References Cited

U.S. PATENT DOCUMENTS

| | | | |
|---|---|---|---|
| 3,799,758 A | 3/1974 | Franz | 71/86 |
| 4,405,531 A | 9/1983 | Franz | 260/501.12 |
| 4,853,026 A | 8/1989 | Frisch et al. | 71/86 |
| 5,034,046 A | 7/1991 | Young | 72/83 |
| 5,118,338 A | 6/1992 | Moller | 71/86 |
| 5,178,795 A | 1/1993 | Roberts | 252/356 |
| 5,180,414 A | 1/1993 | Darchy et al. | 504/206 |
| 5,206,021 A | 4/1993 | Dookhith et al. | 424/405 |
| 5,234,919 A | 8/1993 | Roberts | 514/119 |
| 5,254,344 A | 10/1993 | Dookhith et al. | 424/405 |
| 5,302,579 A | 4/1994 | Young | 504/206 |
| 5,393,791 A | 2/1995 | Roberts | 514/762 |
| 5,464,807 A | 11/1995 | Claude et al. | 504/206 |
| 5,561,099 A | 10/1996 | Murphy et al. | 504/116 |
| 5,580,567 A | 12/1996 | Roberts | 424/405 |
| 5,668,085 A | 9/1997 | Forbes et al. | 504/206 |
| 5,710,104 A | 1/1998 | Magin et al. | 504/206 |
| 5,725,630 A | 3/1998 | Roberts et al. | 71/11 |
| 5,741,502 A | 4/1998 | Roberts | 424/405 |
| 5,877,112 A | 3/1999 | Roberts et al. | 504/116 |
| 5,906,961 A | 5/1999 | Roberts et al. | 504/116 |
| 6,083,875 A | 7/2000 | Sato et al. | 504/127 |
| 6,200,929 B1 | 3/2001 | Horibe et al. | 504/127 |
| 6,232,272 B1 | 5/2001 | Roberts et al. | 504/323 |
| 6,383,984 B1 | 5/2002 | Aven | 504/116.1 |
| 6,383,987 B1 | 5/2002 | von der Heyde et al. | 504/271 |

FOREIGN PATENT DOCUMENTS

| | | |
|---|---|---|
| WO | 92 12637 | 8/1992 |
| WO | 94 10844 | 5/1994 |
| WO | 09819544 | 5/1998 |
| WO | 09927781 | 6/1999 |
| WO | 018236 | 4/2000 |

OTHER PUBLICATIONS

Turner, D. J. "Effects on glyphosate performance of formulation, additives and mixing with other herbicides". Chapter 15 in The Herbicide Glyphosate. Grossbard et al, ed. 1985.*

McCutcheon's Emulsifiers and Detergents, North American Edition, 2000.

Database CA Online! Chemical Abstracts Service, Columbus, Ohio, US; Turner, D.J. et al. "Complexing agents as herbicide additives" retrieved from STN, Database accession No. 89:158688, XP002188260 abstract & Weed Res. (1978), 18(4), 199–207.

PCT Search Report.

* cited by examiner

*Primary Examiner*—S. Mark Clardy
(74) *Attorney, Agent, or Firm*—Connolly Bove Lodge & Hutz LLP

(57) ABSTRACT

The invention pertains to a method for manufacture and use of a herbicidal formulation containing the free acid form of glyphosate and an acid. Specifically, phosphoric, citric, acetic, propionic, and phosphorous acid and their corresponding salts have been useful in this application. The acid based formulations offer lower glyphosate use rates than standard formulations.

61 Claims, No Drawings

MANUFACTURE AND USE OF A HERBICIDE FORMULATION

RELATED APPLICATION

This application claims benefit to U.S. provisional application 60/223,390 filed Aug. 7, 2000 and incorporates by reference in its entirety U.S. provisional application 60/223,390.

BACKGROUND OF THE INVENTION

Glyphosate is a broad-spectrum herbicide useful in both non-selective and, with the advent of glyphosate tolerant crops, selective weed control. It is generally non-selective and is very effective on deep-rooted perennial species and on annual and biennial species of grasses, sedges and broadleaf weeds. By modifying the genetic make-up of some plant species, various crops can now be grown with resistance to glyphosate herbicidal activity. It is critical that new formulations of glyphosate do not injure these genetically modified plants.

Glyphosate preferably refers to the following compounds:

Glyphosate acid

$HOCOCH_2NHCH_2P(OH)_2$,

Glyphosate-trimesium

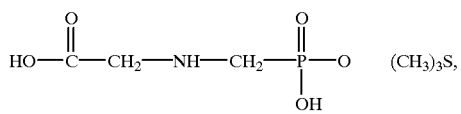

Glufosinate

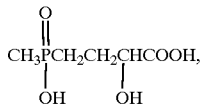

And derivatives thereof.

The solubility of glyphosate acid is relatively low in water (about 1 to about 2%). Since glyphosate is an acid, however, numerous water-soluble salts can be formed. In U.S. Pat. Nos. 4,405,531 and 3,799,758, Franz discusses numerous glyphosate derivatives and homologues, including halogen, hydroxy, thio, ammonium, mono- and di-alkylamine, hydroxy-alkyl and alkenyl amine, hydrocarbyl, hydrocarbonoxyhydrocarbyl, halohydrocarbyl, and halohydrocarbonoxyhydrocarbyl, esters and tioesters, aminohydrocarbyl, metallo-oxy including alkali and alkaline earth, copper, zinc, manganese and nickel-oxy, aminoxy, organic aminoxy, and/or strong acid salt derivatives and homologues. According to Franz, the alkali, alkaline earth, ammonium and organic amine salts are preferred.

Ammonia, potassium, isopropylamine, and sesquisodium salts of glyphosate have been used in the past to enhance water solubility. Isopropylamine is the most common of these amine salts. Monsanto Chemical Company's Trademarked ROUNDUP® Herbicide is an example of an Isopropylamine salt of glyphosate. Monsanto Chemical Company's Trademarked ROUNDUP® DRY PAK is an example of a dry ammonium salt of glyphosate. Zeneca Ag Products' Trademarked TOUCHDOWN® is an example of a diammonium salt of glyphosate.

Numerous patents have been granted to protect formulations of glyphosate and it's salts. Generally, these formulations offer more effective applications of the herbicide. A few examples of patented glyphosate formulations are discussed here. In U.S. Pat. No. 5,668,085, Forbes et al., describes formulations of glyphosate containing alkoxylated amine surfactants. In U.S. Pat. No. 5,710,104, Magin et al., describes glyphosate compositions containing polyethoxylated monohydric primary alcohol. In U.S. Pat. No. 5,464,807, Claude et al., describes unique formulations of glyphosate and alkoxylated quaternary ammonium surfactants. U.S. Pat. No. 5,118,338 describes a formulation containing glyphosate acid and dry surfactant. This final formulation is a dry product.

In U.S. Pat. No. 5,302,579, Young describes a glyphosate acid formulation containing sulfuric acid and optionally a chalcogen compound. Young further instructs that hydrochloric acid does not form soluble reaction products with glyphosate. Sulfuric acid and hydrochloric acid can bring undesirable effects on plant tissue. In U.S. Pat. No. 5,034,046, Young actually discloses the use of a formulation of sulfuric acid and urea to control vegetation. With the use of glyphosate over the top of genetically modified crops, phytotoxicity is not acceptable.

Darchy et al., teaches in U.S. Pat. No. 5,180,414 the use of a glyphosate formulation containing phosphate ester surfactants of the formula:

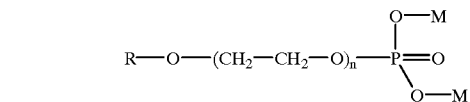

Wherein R is an alkl radical having 4 to 12 carbon atoms, n is an integer from 2 to 10 and M is hydrogen, sodium, ammonium or alkylammonium.

Darchy at col. 3 warns against formulations with too much acidity and reports that they may precipitate the glyphosate.

Sato et al., teaches in U.S. Pat. No. 6,083,875 the use of phosphated solvents having a water solubility of less than 1%. His preferred embodiments are triaryl phosphates and formulations minimize the level of these phosphated solvents.

Frisch et al., teaches in U.S. Pat. No. 4,853,026 the use of ethoxylated acidic phosphoric acid esters. These formulations contain at least 2 herbicides and use phosphate esters as surfactants/emulsifiers.

Horibe et al., teaches in WO018236A1, WO9819544A1 and U.S. Pat. No. 6,200,929 the use of phosphorous acid derivatives in combination with glyphosate. The phosphorous acid derivative is of the following structure:

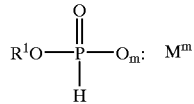

wherein $R^1$ represents a $C_{1-8}$ alkyl group (said alkyl group may be substituted with 1 to 3 halogen atoms or 1 to 3, $C_{1-3}$ alkoxy groups), a phenyl group or a benzyl group; M represents a hydrogen atom, an ammonium group (said ammonium group may be substituted with 1 to 4 $C_{1-3}$ alkyl groups), a sodium atom, a potassium atom, a lithium atom, a magnesium atom, a calcium atom, a barium atom, a zinc atom, a manganese atom, a copper atom, an iron atom, a nickel atom or an aluminum atom; and m stands for an integer equivalent to the positive valency of M. $R^1$ is not taught to be only H. The phosphorous acid must be a derivative and not phosphorous acid alone.

Maier teaches in WO9927781A1 the use of phosphate esters in combination with other surfactants for use in glyphosate formulations.

SUMMARY OF THE INVENTION

We have surprisingly discovered that phosphoric and phosphorous acids can be used to dissolve Glyphosate acid. These acid-solubolized formulations have further been discovered to dramatically improve the herbicidal effectiveness of glyphosate. Furthermore, we have discovered that salts of these acids and organic carboxylic acids can be used to dissolve glyphosate.

The invention relates to a herbicidal composition comprising
(a) Glyphosate in the free acid form,
(b) at least one acid component selected from the group consisting of
 (1) phosphoric acid,
 (2) phosphorous acid ($H_3PO_3$),
 (3) a neutralized organic acid,
 (4) salts of phosphoric acid and
 (5) salts of phosphorous acid and optionally (c) a surfactant.

DETAILED DESCRIPTION OF THE INVENTION

The invention relates to a herbicidal composition comprising
(a) glyphosate in the free acid form,
(b) at least one acid component selected from the group consisting of
 a. phosphoric acid,
 b. phosphorous acid ($H_3PO_3$),
 c. a neutralized organic acid,
 d. salts of phosphoric acid and
 e. salts of phosphorous acid and optionally (c) a surfactant.

The water solubility of Glyphosate is approximately 1.2%. Using phosphoric, acetic, citric, propionic, and phosphorous acids, glyphosate can be solubolized at as much as about 20 to about 30% in the acid. The formulation will contain from about 1 to about 30% of glyphosate acid. The preferred embodiment of this formulation will contain about 5 to about 25% glyphosate acid. The most preferred embodiment of this formulation contains about 5 to about 20% glyphosate acid.

Phosphoric acid and phosphorous acid are significantly different than the phosphoric acid esters (also known as phosphate esters) and the phosphorous acid derivatives discussed in the prior art. In the context of this invention, the phosphate esters are surfactants and not an acid component. Phosphoric acid esters are surfactants that are well known for their emulsifying ability in high electrolyte solutions such as fertilizers. Optionally, the acids can be neutralized to form stable formulations.

The formulation will contain about 1 to about 99% of phosphoric acid ($H_3PO_4$), acetic acid, citric acid, propionic acid, or phosphorous acid ($H_3PO_3$). Combinations of these acids can also be used. The preferred embodiment of this formulation will contain about 40 to about 99%, preferably about 50 to about 99% of phosphoric, phosphorous, citric, propionic or acetic acid. The most preferred embodiment will contain about 80 to about 90% of phosphoric, phosphorous, citric, propionic, or acetic acid.

The phosphoric acid or phosphorous acids can be neutralized without losing solubility of the glyphosate acid. Preferably, the acid will be neutralized with ammonia ($NH_3$), Potassium (K) or Sodium (Na). Most preferably, the phosphoric, phosphorous, citric, propionic or acetic acids can be neutralized with potassium or ammonia.

Preferably the organic acid is neutralized to make either an ammonia or potassium salt of the organic acid and preferably said herbicidal composition has a pH or less than about 6.0, more preferably a pH of less than 5.0, more preferably a pH of less than 4.0 and most preferably a pH of less than 4.0.

The salts of phosphoric acid and the salts of phosphorous acid are preferably ammonia or potassium salts of phosphoric acid or phosphorous acid and said herbicidal composition has a pH or less than about 6.0 more preferably a pH of less than 5.0, more preferably a pH of less than 4.0 and most preferably a pH of less than 4.0.

The formulation can be further enhanced with the addition of a surfactant component. The surfactant can be any known to reduce the surface tension of water by at least 5 dynes/cm. The surfactant can be present at 1% w/w in water, reduces the surface tension of water to less than 60 dynes.

Useful surfactants include but are not limited to:
Alcohol alkoxylates including but not limited to:
 Based on branched and linear alcohols
 Those containing ethylene oxide or propylene oxide
Alcohol alkoxylate sulfates,
Alkylphenol alkoxylates including but not limited to:
 Nonylphenol and octylphenols.
 Those containing ethylene oxide or propylene oxide
Alkanolamides,
Alkylaryl sulfonates,
Amine oxides
Amines including but not limited to:
 Fatty amine alkoxylates such as but not limited to tallowamine alkoxylates,
Betaine derivatives,
Block polymers of ethylene and propylene glycol,
Carboxylated alcohol or alkylphenol alkoxylates,
Diols, including but not limited to Butanediols,
Diphenyl sulfonate derivatives,
Ethers, including but not limited to
 Butyl celluslove,
 Butyl carbitol,
Ethoxylated amines,
Ethoxylated fatty acids,
Ethoxylated fatty esters and oils,
Ethylene carbonate,
Fatty esters,
Glycerol esters,
Glycols including but not limited to
 Propylene glycol,
 Ethylene glycol,
 Dipropylene glycol,
 Diethylene glycol,
Phosphate ester surfactants including but not limited to
 Phosphate esters of alcohol alkoxylates,
 Phosphate esters of alkylphenol alkoxylates,
Propylene Carbonate,
Sarcosine derivatives,
Silicone-based surfactants,
Sorbitan derivatives including but not limited to:
 Sorbitan esters,
 Alkoxylated sorbitan esters, Sucrose and glucose derivatives including but not limited to:
  Alkylpolyglucosides,
Sulfates and sulfonates of alkoxylated alkylphenols,
Sulfates of alcohols,
Tristyrylphenol Alkoxylates,
Other surfactants are disclosed in McCutcheon's Emulsifiers and Detergents, North American Edition, 2000.
Other surfactants are disclosed in the following patents:
  U.S. Pat. No. 5,741,502 Homogeneous, essentially non-aqueous adjuvant compositions with buffering capability
  U.S. Pat. No. 5,725,630 Dry granular fertilizer blend and a method of fertilizing plants
  U.S. Pat. No. 5,580,567 Homogeneous, essentially non-aqueous adjuvant compositions with buffering capability
  U.S. Pat. No. 5,393,791 Homogeneous, essentially non-aqueous adjuvant compositions with buffering capability
  U.S. Pat. No. 5,234,919 Water soluble, highly active dimethoate formulations in an alcohol/ester solvent system
  U.S. Pat. No. 5,178,795 Homogeneous, essentially non-aqueous adjuvant compositions with buffering capability
  U.S. Pat. No. 5,906,961 Alkanolamide spreader-sticker surfactant combination
  U.S. Pat. No. 5,877,112 Agricultural formulation
  U.S. Pat. No. 6,232,272 Manufacture and use of herbicide chlorinated phenoxy formulation All the references described herein are incorporated by reference in its entirety for all useful purposes.

The herbicidal composition can contain less than about 15% by weight water. The herbicidal composition preferably has a ratio of acid to glyphosate of at least about 2:1 and at most about 99:1.

The formulations described herein are intended for use in aqueous based systems. The pesticide applicator will generally dilute the herbicide formulation with water or aqueous fertilizers to apply to plants.

EXAMPLE 1

A formula was prepared using the formula shown here:

| Ingredients | % |
| --- | --- |
| Phosphoric acid (85%) | 83.0 |
| Phosphate ester of an alcohol Ethoxylate | 5.0 |
| Glyphosate acid technical (95%) | 12.0 |

This formula produced a clear liquid formulation that was stable at hot and cold temperatures.

EXAMPLE 2

A weed control experiment was conducted to compare the effect of the formula in Example 1 to commercially available glyphosate formulations. ROUNDUP ULTRA® from Monsanto Chemical Company was used as the commercially available glyphosate. ROUNDUP UILTRA® contains 41% of the isopropylamine salt or the equivalent of 30.4% of the glyphosate acid. The commercial rate of this product is typically 32 ounces per acre. RODEO® from Monsanto Chemical Company was used as another commercially available form of glyphosate. RODEO® contains 53.8% of the isopropylamine salt of glyphosate or the equivalent of about 39.8% of the glyphosate acid. The commercial rate of this product is typically 32 to 64 ounces per acre. The formulation from Example 1 was tested at 32 ounces per acre. All treatments were applied in 10 gallons of total spray carrier (water) per acre. As seen in the chart below, the herbicidal activity was as good or better using the experimental formula from Example 1 as the commercial rates of ROUNDUP ULTRA® and RODEO®.

| Formulation | Rate of formulated product per acre | Grams of Glyphosate Acid A.I. per acre | % control by weed species (5 days after treatment) | | |
| --- | --- | --- | --- | --- | --- |
| | | | Giant foxtail | Common waterhemp | Velvetleaf |
| ROUNDUP ULTRA ® | 1 quart | 340.2 | 73.8 | 72.5 | 65.0 |
| RODEO ® | 1 quart | 340.2 | 73.8 | 68.8 | 61.3 |
| RODEO ® | 2 quarts | 680.4 | 75.0 | 71.3 | 66.3 |
| Example 1 | 1 quart | 175.7 | 72.5 | 68.8 | 65.0 |

EXAMPLE 3

A second weed control experiment was conducted to compare the effect of the formula in Example 1 to commercially available glyphosate formulations. All treatments were applied in 10 gallons of total spray carrier (water) per acre. As seen in the chart below, the herbicidal activity was as good or better using the experimental formula from Example 1 as the commercial rates of ROUNDUP ULTRA® and RODEO®.

| Formulation | Rate of formulated product per acre | Grams of Glyphosate Acid A.I. per acre | % control by weed species (5 days after treatment) | | |
| --- | --- | --- | --- | --- | --- |
| | | | Giant foxtail | Giant ragweed | Lambsquarters |
| ROUNDUP ULTRA ® | 1 quart | 340.2 | 55.0 | 57.5 | 58.8 |
| RODEO ® | 1 quart | 340.2 | 52.5 | 56.3 | 46.3 |
| RODEO ® | 2 quarts | 60.0 | 63.8 | 55.0 | 66.3 |
| Example 1 | 1 quart | 175.7 | 61.3 | 56.3 | 51.3 |

EXAMPLE 4

The formula below was prepared, which should provide herbicidal activity, fungicidal activity, and fertilizer activity. Phosphorous acid is a fertilizer that is widely believed to have fungicidal properties as well. This formulation was also found to be stable at cold and hot storage conditions.

| Ingredients | % |
| --- | --- |
| Phosphorous acid (65%) | 85.0 |
| Glyphosate acid technical (95%) | 15.0 |

EXAMPLES 5 (a and b)

The formulas below were prepared, and although both produced clear solutions, and both should provide herbicidal activity, they present an unacceptable risk with regards to phytotoxicity or plant injury. Hydrochloric acid and sulfuric acid are used to consume plant tissue in some analytical methods.

|  | % |
|---|---|
| Ingredients 5(a) | |
| Sulfuric acid (98%) | 85.0 |
| Glyphosate acid technical (95%) | 15.0 |
| Ingredients 5(b) | |
| Hydrochloric acid (37%) | 85.0 |
| Glyphosate acid technical (95%) | 15.0 |

EXAMPLE 6

The formula below was prepared, which should provide herbicidal activity and fertilizer activity. Phosphoric acid is a widely used fertilizer. This formulation was also found to be stable at cold and hot storage conditions.

| Ingredients | % |
|---|---|
| Phosphoric acid (85%) | 85.0 |
| Glyphosate acid technical (95%) | 15.0 |

EXAMPLE 7

The formula below was prepared, which should provide herbicidal activity and fertilizer activity. Ammonia is a widely used fertilizer. This formulation was also found to be stable at cold and hot storage conditions.

| Ingredients | % |
|---|---|
| Ammonia acetate (45%) | 85.0 |
| Glyphosate acid technical (95%) | 15.0 |

EXAMPLE 8

The formula below was prepared, which should provide herbicidal activity and fertilizer activity. Ammonia acetate is a useful fertilizer. This formulation was also found to be stable at cold and hot storage conditions.

| Ingredients | % |
|---|---|
| Ammonia acetate (60%) | 90.0 |
| Glyphosate acid technical (95%) | 10.0 |

The invention can be practiced with substantially no or no sulfuric acid present or substantially no or no chalcogen compound present as discussed in Young above.

The invention can be practiced without the use of the amine surfactants described in U.S. Pat. No. 5,668,085. These amine surfactants have the following formula:

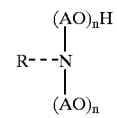

wherein R represents a straight- or branched-chain alkyl or alkenyl group having from about 8 to about 22 carbon atoms, A represents an alkylene group, for example an ethylene or propylene group, and n and n' are integers such that n+n' has a value of about 2 to about 8, (ii) a mixture of such amines having different groups R, the average number of carbon atoms in the groups R being from about 8 to about 22, or (iii) a mixture of such amines having different values of n and n', n and n' being integers such that the average value of n+n' in the mixture is about 2 to about 8, R having a single value or an average value as in a mixture (ii).

The invention can also be practiced without the use of water-soluble polyethoxylated monohydric primary alcohol having a β-branched alkyl group which has a total of at least about 10 carbon atoms and at least about 3 carbon atoms in the branch on the a β-carbon atom or agriculturally acceptable salt or ester thereof. This is a required ingredient in U.S. Pat. No. 5,710,104.

We claim:

1. A liquid herbicidal concentrate composition comprising
   a. Glyphosate in the free acid form,
   b. at least one acid component selected from the group consisting of
      1. phosphoric acid,
      2. phosphorous acid ($H_3PO_3$),
      3. a neutralized organic acid,
      4. salts of phosphoric acid and
      5. salts of phosphorous acid and
   optionally (c) a surfactant.

2. The herbicidal composition as claimed in claim 1, comprising glyphosate in the free acid form and phosphoric acid.

3. The herbicidal composition as claimed in claim 2, which further comprises a surfactant which at 1% w/w in water, reduces the surface tension of water to less than 60 dynes.

4. The herbicidal composition as claimed in claim 2, which contains less than about 15% by weight water.

5. The herbicidal composition as claimed in claim 2, comprising a ratio of said phosphoric acid to said glyphosate of at least 2:1 and at most 99:1.

6. The herbicidal composition as claimed in claim 1, comprising glyphosate glyphosate in the free acid form and phosphorous acid.

7. The herbicidal composition as claimed in claim 6, which further comprises a surfactant which at 1% w/w in water, reduces the surface tension of water to less than 60 dynes.

8. The herbicidal composition as claimed in claim 6, which contains less than 15% water.

9. The herbicidal composition as claimed in claim 6, comprising a ratio of said phosphorous acid to said glyphosate of at least about 2:1 and at most about 99:1.

10. The herbicidal composition as claimed in claim 1, comprising glyphosate glyphosate in the free acid form and a neutralized organic acid.

11. The herbicidal composition as claimed in claim 10, in which the organic acid is neutralized to make either an ammonium or potassium salt of the organic acid and said herbicidal composition has a pH or less than about 6.0.

12. The herbicidal composition as claimed in claim 10, in which the organic acid is neutralized to make either an ammonium or potassium salt of the organic acid and said herbicidal composition has a pH or less than about 5.0.

13. The herbicidal composition as claimed in claim 10, in which the organic acid is neutralized to make either an ammonium or potassium salt of the organic acid and said herbicidal composition has a pH or less than about 4.0.

14. The herbicidal composition as claimed in claim 10, in which the organic acid is citric acid or acetic acid.

15. The herbicidal composition as claimed in claim 1, comprising (a) glyphosate glyphosate in the free acid form and (b) ammonium or potassium salts of phosphoric acid and said herbicidal composition has a pH or less than about 6.0.

16. The herbicidal composition as claimed in claim 1, comprising (a) glyphosate glyphosate in the free acid form and (b) ammonium or potassium salts of phosphoric acid and said herbicidal composition has a pH or less than about 5.0.

17. The herbicidal composition as claimed in claim 1, comprising (a) glyphosate glyphosate in the free acid form and (b) ammonium or potassium salts of phosphoric acid and said herbicidal composition has a pH or less than about 4.0.

18. The herbicidal composition as claimed in claim 15, wherein said phosphoric acid is a neutralized phosphoric acid.

19. The herbicidal composition as claimed in claim 1, comprising glyphosate glyphosate in the free acid form and ammonium or potassium salts of phosphorous acid and said herbicidal composition has a pH or less than about 6.0.

20. The herbicidal composition as claimed in claim 1, comprising glyphosate glyphosate in the free acid form and ammonium or potassium salts of phosphorous acid and said herbicidal composition has a pH or less than about 5.0.

21. The herbicidal composition as claimed in claim 1, comprising glyphosate glyphosate in the free acid form and ammonium or potassium salts of phosphorous acid and said herbicidal composition has a pH or less than about 4.0.

22. The herbicidal composition as claimed in claim 19, wherein said phosphorous acid is a neutralized phosphorous acid.

23. The herbicidal composition as claimed in claim 1, wherein if a phosphorous acid is used, then there is no antioxidant present.

24. The herbicidal composition as claimed in claim 1, wherein the composition does not contain amine surfactants which have the following formula:

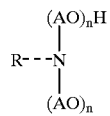

wherein R represents a straight- or branched-chain alkyl or alkenyl group having from about 8 to about 22 carbon atoms, A represents an alkylene group, for example an ethylene or propylene group, and n and n' are integers such that n+n' has a value of about 2 to about 8, (ii) a mixture of such amines having different groups R, the average number of carbon atoms in the groups R being from about 8 to about 22, or (iii) a mixture of such amines having different values of n and n', n and n' being integers such that the average value of n+n' in the mixture is about 2 to about 8, R having a single value or an average value as in a mixture (ii).

25. The herbicidal composition as claimed in claim 1, wherein the composition does not contain sulfuric acid.

26. The herbicidal composition as claimed in claim 1, wherein the composition contains a surfactant.

27. The herbicidal composition as claimed in claim 26, wherein the surfactant is Alcohol alkoxylate,
Alcohol alkoxylate sulfate,
Alkylphenol alkoxylate,
Alkanolamide,
Alkylaryl sulfonate,
Amine oxide,
Amine,
Betaine derivative,
Block polymers of ethylene and propylene glycol,
Carboxylated alcohol or alkylphenol alkoxylate,
Diol,
Diphenyl sulfonate derivative,
Ether,
Ethoxylated amine,
Ethoxylated fatty acid,
Ethoxylated fatty ester and oils,
Ethylene carbonate,
Fatty ester,
Glycerol ester,
Glycol,
Phosphate ester surfactant,
Propylene Carbonate,
Sarcosine derivative,
Silicone-based surfactant,
Sorbitan derivative,
Sucrose derivative,
glucose derivative,
Sulfate of alkoxylated alkylphenol,
sulfonate of alkoxylated alkylphenol,
Sulfate of alcohol or
Tristyrylphenol Alkoxylate.

28. The herbicidal composition as claimed in claim 26, wherein the surfactant is
A) Alcohol alkoxylate based on branched and linear alcohols containing ethylene oxide or propylene oxide
B) Alcohol alkoxylate sulfate,
C) Nonylphenol alkoxylate containing ethylene oxide,
D) Nonylphenol alkoxylate containing propylene oxide,
E) Octylphenols alkoxylate containing ethylene oxide
F) Octylphenols alkoxylate containing propylene oxide,
G) Fatty amine alkoxylate,
H) Butanediol,
I) Butyl cellulose ether,
J) Butyl carbitol,
K) Propylene glycol,
L) Ethylene glycol,
M) Dipropylene glycol,
N) Diethylene glycol,
O) Phosphate esters of alcohol alkoxylates,
P) Phosphate esters of alkylphenol alkoxylates,
Q) Sorbitan ester,
R) Alkoxylated sorbitan ester or
S) Alkylpolyglucoside.

29. The herbicidal composition as claimed in claim 1, wherein the acid is present in an amount form about 40 to about 99% by weight.

30. The herbicidal composition as claimed in claim 3, which contains less than about 15% by weight water and has a ratio of said phosphoric acid to said glyphosate of at least 2:1 and at most 99:1.

31. The herbicidal composition as claimed in claim 2, wherein the acid is present in an amount form about 50 to about 99% by weight.

32. The herbicidal composition as claimed in claim 30, wherein the acid is present in an amount form about 80 to about 90% by weight.

33. The herbicidal composition as claimed in claim 6, which contains less than about 15% by weight water and has a ratio of said phosphorous acid to said glyphosate of at least 2:1 and at most 99:1.

34. The herbicidal composition as claimed in claim 6, wherein the acid is present in an amount form about 50 to about 99% by weight.

35. The herbicidal composition as claimed in claim 33, wherein the acid is present in an amount form about 80 to about 90% by weight.

36. The herbicidal composition as claimed in claim 10, which contains less than about 15% by weight water and has a ratio of said acid to said glyphosate of at least 2:1 and at most 99:1.

37. The herbicidal composition as claimed in claim 10, wherein the acid is present in an amount form about 50 to about 99% by weight.

38. The herbicidal composition as claimed in claim 36, wherein the acid is present in an amount form about 80 to about 90% by weight.

39. The herbicidal composition as claimed in claim 15, which contains less than about 15% by weight water and has a ratio of acid to glyphosate of at least 2:1 and at most 99:1.

40. The herbicidal composition as claimed in claim 15, wherein the acid is present in an amount form about 50 to about 99% by weight.

41. The herbicidal composition as claimed in claim 36, wherein the acid is present in an amount form about 80 to about 90% by weight.

42. The herbicidal composition as claimed in claim 22, which contains less than about 15% by weight water and has a ratio of said acid to said glyphosate of at least 2:1 and at most 99:1.

43. The herbicidal composition as claimed in claim 22, wherein the acid is present in an amount form about 50 to about 99% by weight.

44. The herbicidal composition as claimed in claim 36, wherein the acid is present in an amount form about 80 to about 90% by weight.

45. The herbicidal composition as claimed in claim 1, wherein the glyphosate is present in an amount form about 1 to about 30% by weight.

46. The herbicidal composition as claimed in claim 1, wherein the glyphosate is present in an amount form about 5 to about 25% by weight.

47. The herbicidal composition as claimed in claim 29, wherein the glyphosate is present in an amount form about 5 to about 20% by weight.

48. The herbicidal composition as claimed in claim 31, wherein the glyphosate is present in an amount form about 5 to about 25% by weight.

49. The herbicidal composition as claimed in claim 32, wherein the glyphosate is present in an amount form about 5 to about 20% by weight.

50. The herbicidal composition as claimed in claim 34, wherein the glyphosate is present in an amount form about 5 to about 25% by weight.

51. The herbicidal composition as claimed in claim 35, wherein the glyphosate is present in an amount form about 5 to about 20% by weight.

52. The herbicidal composition as claimed in claim 37, wherein the glyphosate is present in an amount form about 5 to about 25% by weight.

53. The herbicidal composition as claimed in claim 38, wherein the glyphosate is present in an amount form about 5 to about 20% by weight.

54. The herbicidal composition as claimed in claim 40, wherein the glyphosate is present in an amount form about 5 to about 25% by weight.

55. The herbicidal composition as claimed in claim 41, wherein the glyphosate is present in an amount form about 5 to about 20% by weight.

56. The herbicidal composition as claimed in claim 43, wherein the glyphosate is present in an amount form about 5 to about 25% by weight.

57. The herbicidal composition as claimed in claim 44, wherein the glyphosate is present in an amount form about 5 to about 20% by weight.

58. A herbicidal composition comprising
 a. Glyphosate in the free acid form,
 b. at least one acid component selected from the group consisting of
  i. phosphoric acid,
  ii. phosphorous acid ($H_3PO_3$),
  iii. a neutralized organic acid, and
 c. a surfactant selected from the group consisting of
  Alcohol alkoxylate,
  Alcohol alkoxylate sulfate,
  Alkylphenol alkoxylate,
  Alkanolamide,
  Alkylaryl sulfonate,
  Amine oxide,
  Amine,
  Betaine derivative,
  Block polymers of ethylene and propylene glycol,
  Carboxylated alcohol or alkylphenol alkoxylate,
  Diol,
  Diphenyl sulfonate derivative,
  Ether,
  Ethoxylated amine,
  Ethoxylated fatty acid,
  Ethoxylated fatty ester and oils,
  Ethylene carbonate,
  Fatty ester,
  Glycerol ester,
  Glycol,
  Phosphate ester surfactant,
  Propylene Carbonate,
  Sarcosine derivative,
  Silicone-based surfactant,
  Sorbitan derivative,
  Sucrose derivative,
  glucose derivative,
  Sulfate of alkoxylated alkylphenol,
  sulfonate of alkoxylated alkylphenol,
  Sulfate of alcohol and
  Tristyrylphenol Alkoxylate.

59. The composition as claimed in claim 58, wherein the acid component is phosphorous acid.

60. The composition as claimed in claim 58, wherein the acid component is phosphoric acid.

61. The composition as claimed in claim 58, wherein the composition is a liquid herbicidal concentrate.

* * * * *